(12) United States Patent
Bettencourt-Silva et al.

(10) Patent No.: US 11,694,815 B2
(45) Date of Patent: Jul. 4, 2023

(54) INTELLIGENT RANKING OF SECTIONS OF CLINICAL PRACTICAL GUIDELINES

(71) Applicant: INTERNATIONAL BUSINESS MACHINES CORPORATION, Armonk, NY (US)

(72) Inventors: Joao H. Bettencourt-Silva, Dublin (IE); Natalia Mulligan, Dublin (IE); Marco Luca Sbodio, Castaheany (IE); Theodora Brisimi, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 564 days.

(21) Appl. No.: 16/660,474

(22) Filed: Oct. 22, 2019

(65) Prior Publication Data
US 2021/0118577 A1    Apr. 22, 2021

(51) Int. Cl.
*G16H 70/20*    (2018.01)
*G06N 20/00*    (2019.01)

(52) U.S. Cl.
CPC .............. *G16H 70/20* (2018.01); *G06N 20/00* (2019.01)

(58) Field of Classification Search
None
See application file for complete search history.

(56) References Cited

U.S. PATENT DOCUMENTS

| | | | |
|---|---|---|---|
| 8,185,448 B1 | 5/2012 | Myslinski | |
| 8,645,165 B2 | 2/2014 | Belcher et al. | |
| 2005/0086078 A1 | 4/2005 | Maloney et al. | |
| 2011/0295903 A1 | 12/2011 | Chen | |
| 2014/0141980 A1 | 5/2014 | Stephan et al. | |
| 2016/0140446 A1 | 5/2016 | Adderly et al. | |
| 2016/0154892 A1* | 6/2016 | Carrier | G06F 40/295 707/691 |
| 2016/0328607 A1 | 11/2016 | Krishnan | |
| 2017/0308655 A1 | 10/2017 | Carlson et al. | |
| 2018/0067950 A1 | 3/2018 | Byron et al. | |
| 2018/0181718 A1 | 6/2018 | Zaher | |
| 2019/0147246 A1 | 5/2019 | Bossut et al. | |
| 2020/0176113 A1* | 6/2020 | Megerian | G16H 50/70 |

FOREIGN PATENT DOCUMENTS

CN    101334770 A    12/2008

OTHER PUBLICATIONS

"Are all evidence-based practices alike? Problems in the ranking of evidence." UPSHUR, CMAJ, Sep. 2003, 169 (7) 672-673, (2 Pages).
"The GRADE system for rating clinical guidelines." Kavanagh, PLoS medicine vol. 6, No. 9: Sep. 2009, e1000094. doi:10.1371/journal.pmed.1000094, (5 Pages).

(Continued)

*Primary Examiner* — Amresh Singh
(74) *Attorney, Agent, or Firm* — Griffiths & Seaton PLLC

(57) ABSTRACT

Embodiments for implementing intelligent ranking of sections of clinical practice guidelines by a processor. One or more clinical practice guidelines (CPGs) may be identified and analyzed. A score may be assigned to one or more sections of the CPGs according evidential data identified in one or more data sources. The one or more sections of the CPGs may be ranked according to the scoring.

20 Claims, 6 Drawing Sheets

(56) References Cited

OTHER PUBLICATIONS

"Toward Automated Fact-Checking: Detecting Check-worthy Factual Claims by Claim-buster." Hassan, In Proceedings of the 23rd ACM SIGKDD International Conference on Knowledge Discovery and Data Mining (KDD '17). ACM, pp. 1803-1812, (10 Pages).
"Classifying Recommendations for Clinical Practice Guidelines" American Academy of Pediatrics Pediatrics vol. 114 No. 3 Sep. 2004 (6 Pages).

* cited by examiner

INTELLIGENT RANKING OF SECTIONS OF CLINICAL PRACTICAL GUIDELINES

BACKGROUND OF THE INVENTION

Field of the Invention

The present invention relates in general to computing systems, and more particularly to, various embodiments for intelligent ranking of sections of clinical practice guidelines by a processor.

Description of the Related Art

In today's society, consumers, business persons, educators, and others use various computing network systems with increasing frequency in a variety of settings. The advent of computers and networking technologies have made possible the increase in the quality of life while enhancing day-to-day activities. For example, many individuals require extensive use of technology relating to the health and the medical field.

Computing systems can include an Internet of Things (IoT), which is the interconnection of computing devices scattered across the globe using the existing Internet infrastructure. IoT devices may be embedded in a variety of physical devices or products. As great strides and advances in technologies come to fruition, the greater the need to make progress in these systems advantageous for efficiency and safety such as, for example, for using the vast amount of available data to recognize impacts on a well-being or health of a person.

SUMMARY OF THE INVENTION

Various embodiments for implementing intelligent ranking of sections of clinical practice guidelines sections using one or more processors, are provided. In one embodiment, by way of example only, a method for intelligent ranking of sections of clinical practice guidelines based on evidence, again by a processor, is provided. One or more clinical practice guidelines (CPGs) may be analyzed. A score may be assigned to one or more of the CPG sections according evidential data identified in one or more data sources. The one or more of the sections of CPGs may be ranked according to the scoring.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
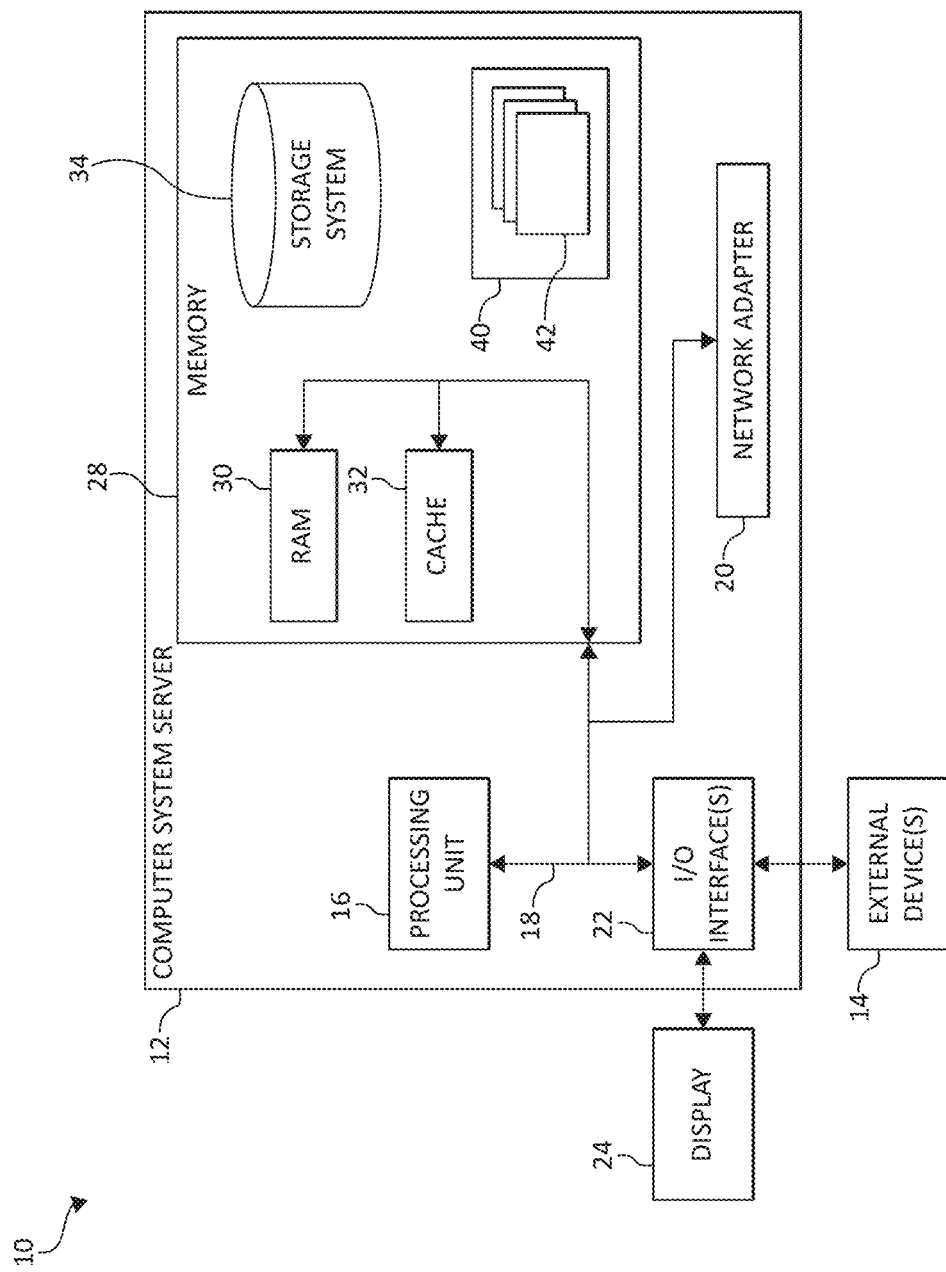
FIG. 1 is a block diagram depicting an exemplary computing node according to an embodiment of the present invention.

Computing systems may include large scale computing called "cloud computing," in which resources may interact and/or be accessed via a communication system, such as a computer network. Resources may be software-rendered simulations and/or emulations of computing devices, storage devices, applications, and/or other computer-related devices and/or services run on one or more computing devices, such as a server. For example, a plurality of servers may communicate and/or share information that may expand and/or contract across servers depending on an amount of processing power, storage space, and/or other computing resources needed to accomplish requested tasks. The word "cloud" alludes to the cloud-shaped appearance of a diagram of interconnectivity between computing devices, computer networks, and/or other computer related devices that interact in such an arrangement.

For example, within the health care industry, clinical practice guidelines ("CPGs") may be used by various types of health professionals. In one aspect, evidence-based health care/medicine and evidence-based policies are approaches in the health care industry.

A CPG may be a set of recommendations, actions and goals that support physicians/health care professions making decisions to improve health service delivery and outcomes. In an additional aspect, a CPG may be statements that include recommendations intended to optimize user/patient care that may be informed by a systematic review of evidence and an assessment of the benefits and harms of alternative care options. Thus, a CPG may offer an evaluation of a quality of relevant scientific literature, and an assessment of the likely benefits and harms of a particular treatment. This information enables health care clinicians to select a "best care" or "appropriate care" for a unique patient.

The CPGs may also include any other evidence-based documents that describe a set of recommendations, instructions or tasks. For example, a local hospital protocol for management of patients with norovirus, a set of recommendations derived from the results of a clinical trial or a research paper with such similar information. A section of a CPG may refer to a particular recommendation or action described in the guideline. A CPG is a collection of multiple recommendations. For example: "measure blood pressure at least once every 12 months" is a recommendation of the Type 2 Diabetes guideline (NICE guideline NG28). It should be noted that as user herein, the "recommendation" may relate to a section of a CPG document (e.g., one or more paragraphs) describing instructions, steps, operations, protocols, and/or tasks intended to advise patient care (e.g., optimize the health state of a user). Also, one or more aspects of the present invention may apply to any other evidence-based documents that describe a set of recommendations, instructions or tasks.

As used herein, the terms "Clinical Practice Guidelines," "Clinical Guidelines," "Guidelines," and "Clinical Pathways" may be used interchangeably. It should be noted, as used herein, the term "patient" may be used interchangeably with the terms "user." The patient profile may include a collection of historical data (e.g., electronic data from one or more electronic health care records) that may be related to one or more medical conditions of a user.

Effective CPG may be used, for example, to: 1) reduce disparities in healthcare delivery (e.g., there may be variabilities between regional and provider-level clinical care leading to poor outcomes and added costs that could be avoided by adhering to one or more CPGs, and 2) reduce the burden that health care professionals currently faces to stay current on, and adhere to, the increasing amounts of medical evidence. Adhering to a CPG may improve healthcare in theory, but guidelines may fail to address local constraints and knowledge (e.g., available in electronic health records (EHRs)).

However, developing CPGs is a complex process that involves several domain experts and practitioners. For example in the healthcare domain, some healthcare organizations may provide a manual describing processes and methods to develop a CPG. In so doing, two important steps in the development of a CPG are required such as, for example: 1) identifying the evidence: literature searching and evidence submission, and 2) reviewing research evidence.

Accordingly, various embodiments are provided herein for intelligent ranking of sections of clinical practice guidelines to support practitioners in reviewing and improving the results of the 1) identifying the evidence: literature searching and evidence submission, and 2) reviewing research evidence by ranking each section of a guideline based on evidence from literature. In one aspect, one or more clinical practice guidelines (CPGs) and data sources (may be analyzed. That is, selected portions or sections of clinical practice guidelines (CPGs) may be identified for analysis. A score may be assigned to one or more of the sections of CPGs according evidential data identified in one or more data sources. The one or more of the sections of CPGs may be ranked according to the scoring.

It should be noted that one or more calculations may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

In general, "best," "appropriate," and/or "optimize" may be used herein interchangeable and refer to and/or defined as "maximize," "minimize," or attain one or more specific targets, objectives, goals, or intentions. "Best," "appropriate," and/or "optimize" may also refer to maximizing a benefit to a user (e.g., maximize a health state/patient profile). "Best," "appropriate," and/or "optimize" may also refer to making the most effective or functional use of a situation, opportunity, or resource.

Additionally, "best," "appropriate," and/or "optimize" may need not refer to a best solution or result but may refer to a solution or result that "is good enough" for a particular application, for example.

It should be noted that reference to calculating an 'interpreted appropriateness" against a predetermined threshold herein following may refer to implementations of a wide variety of metric analysis, data analytics, and other data processing as one of ordinary skill in the art will appreciate. For example, a predetermined threshold may be set as a numerical value, where certain kinds of sections of one or more CPGs associated with a current patient pathway are given certain weighted values, and an aggregate number of the weighted values may be compared against a numerical threshold value.

It should be noted as described herein, the term "cognitive" (or "cognition") may be relating to, being, or involving conscious intellectual activity such as, for example, thinking, reasoning, or remembering, that may be performed using a machine learning. In an additional aspect, cognitive or "cognition may be the mental process of knowing, including aspects such as awareness, perception, reasoning and judgment. A machine learning system may use artificial reasoning to interpret data from one or more data sources (e.g., sensor-based devices or other computing systems) and learn topics, concepts, and/or processes that may be determined and/or derived by machine learning.

In an additional aspect, cognitive or "cognition" may refer to a mental action or process of acquiring knowledge and understanding through thought, experience, and one or more senses using machine learning (which may include using sensor-based devices or other computing systems that include audio or video devices). Cognitive may also refer to identifying patterns of behavior, leading to a "learning" of one or more events, operations, or processes. Thus, the cognitive model may, over time, develop semantic labels to apply to observed behavior and use a knowledge domain or ontology to store the learned observed behavior. In one embodiment, the system provides for progressive levels of complexity in what may be learned from the one or more events, operations, or processes.

In additional aspect, the term cognitive may refer to a cognitive system. The cognitive system may be a specialized computer system, or set of computer systems, configured with hardware and/or software logic (in combination with hardware logic upon which the software executes) to emulate human cognitive functions. These cognitive systems apply human-like characteristics to convey and manipulate ideas which, when combined with the inherent strengths of digital computing, can solve problems with a high degree of accuracy (e.g., within a defined percentage range or above an accuracy threshold) and resilience on a large scale. A cognitive system may perform one or more computer-implemented cognitive operations that approximate a human thought process while enabling a user or a computing system to interact in a more natural manner. A cognitive system may comprise artificial intelligence logic, such as natural language processing (NLP) based logic, for example, and machine learning logic, which may be provided as specialized hardware, software executed on hardware, or any combination of specialized hardware and software executed on hardware. The logic of the cognitive system may implement the cognitive operation(s), examples of which include, but are not limited to, question answering, identification of related concepts within different portions of content in a corpus, and intelligent search algorithms, such as Internet web page searches.

In general, such cognitive systems are able to perform the following functions: 1) Navigate the complexities of human language and understanding; 2) Ingest and process vast amounts of structured and unstructured data; 3) Generate and evaluate hypotheses; 4) Weigh and evaluate responses that are based only on relevant evidence; 5) Provide situation-specific advice, insights, estimations, determinations, evaluations, calculations, and guidance; 6) Improve knowledge and learn with each iteration and interaction through machine learning processes; 7) Enable decision making at the point of impact (contextual guidance); 8) Scale in proportion to a task, process, or operation; 9) Extend and magnify human expertise and cognition; 10) Identify resonating, human-like attributes and traits from natural language; 11) Deduce various language specific or agnostic attributes from natural language; 12) Memorize and recall relevant data points (images, text, voice) (e.g., a high degree of relevant recollection from data points (images, text, voice) (memorization and recall)); and/or 13) Predict and sense with situational awareness operations that mimic human cognition based on experiences.

Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment and/or computing systems associated with one or more vehicles. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random-access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
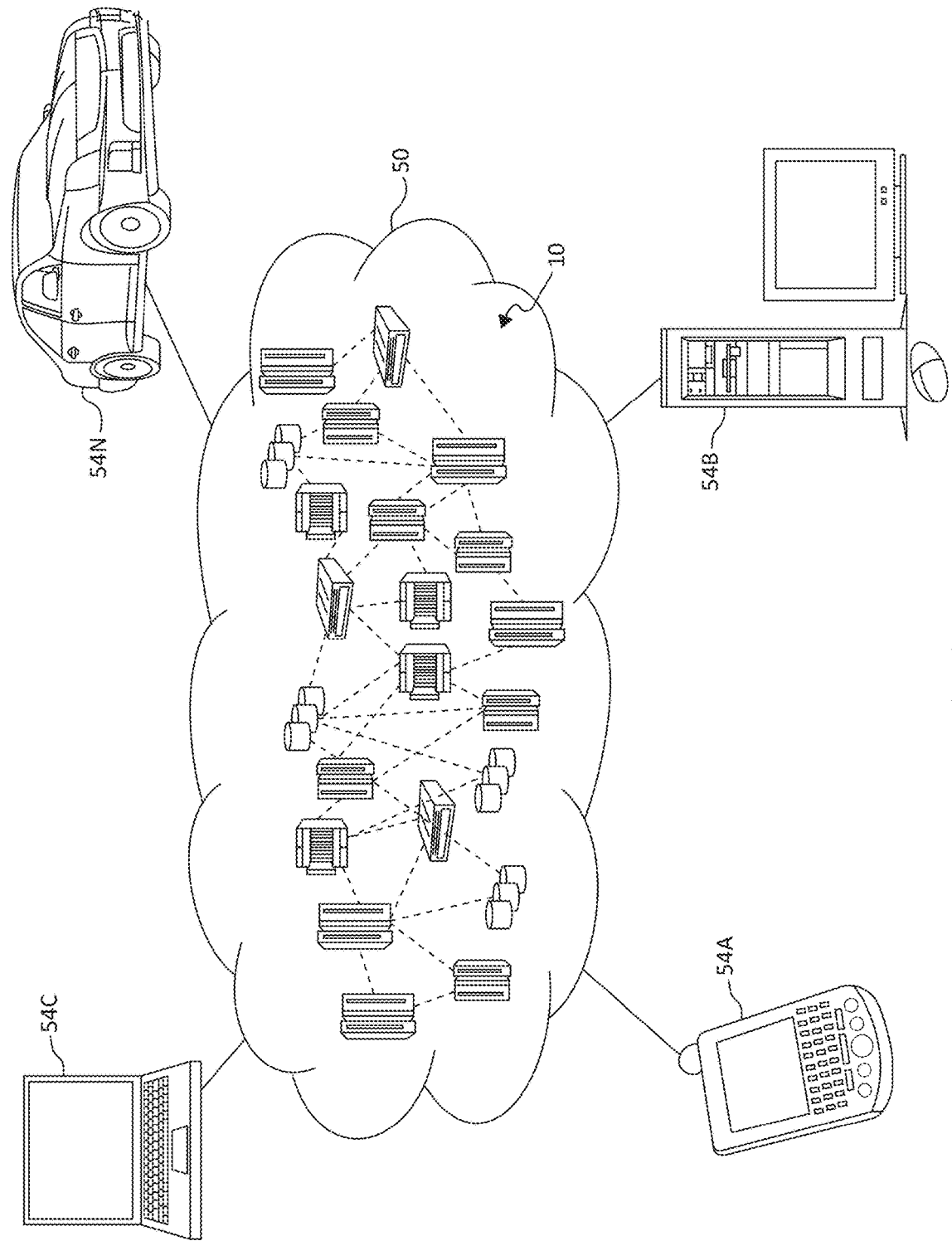
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
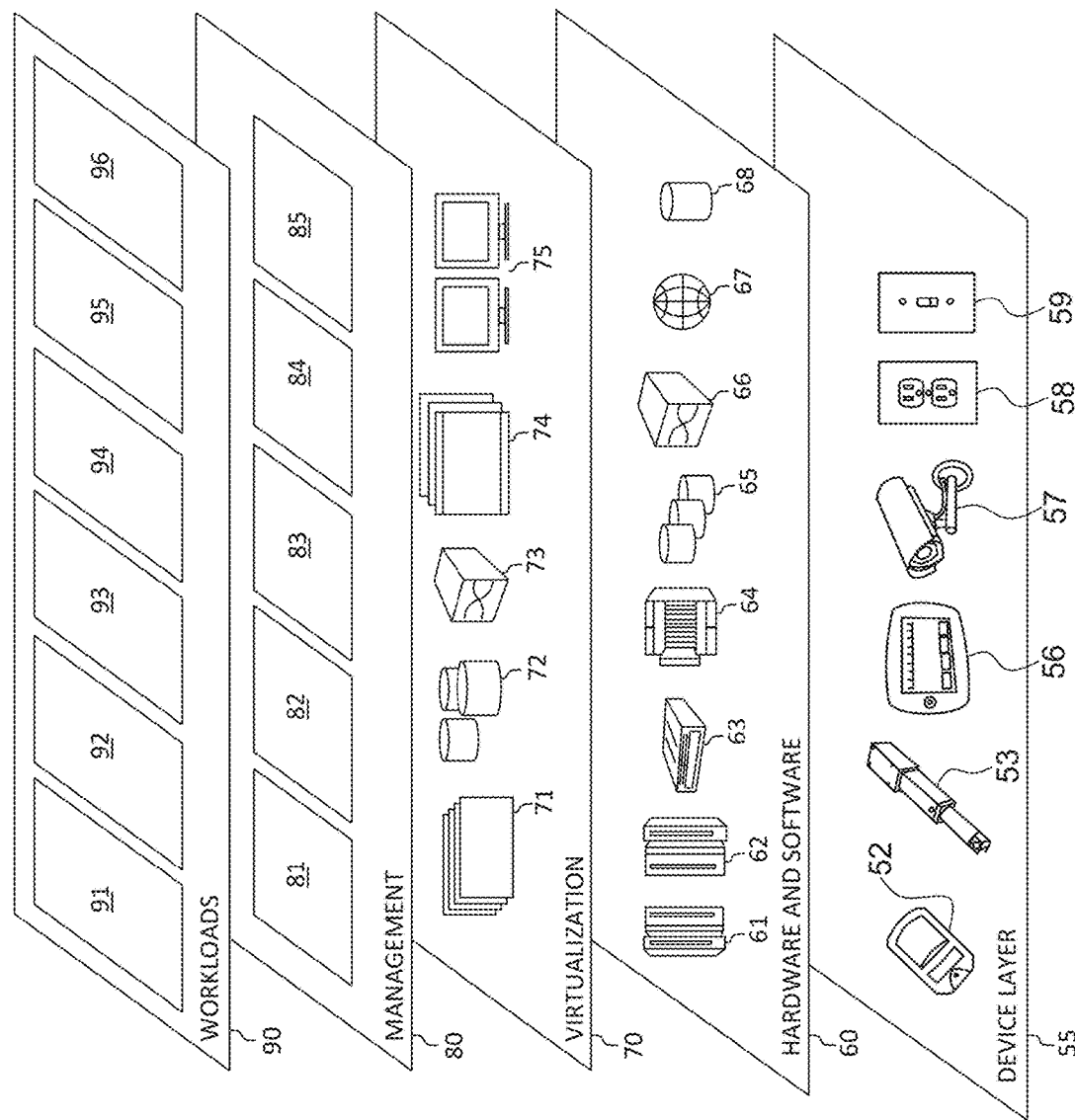
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances and a wide variety of other possible interconnected objects.

Hardware and software layer 60 may include hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for intelligent ranking of sections of CPGs based on evidence. In addition, workloads and functions 96 for intelligent ranking of sections of CPGs based on evidence may include such operations as data analytics, data analysis, and as will be further described, notification functionality. One of ordinary skill in the art will appreciate that the workloads and functions 96 for intelligent ranking of sections of CPGs based on evidence may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously mentioned, the mechanisms of the illustrated embodiments provide novel approaches for the intelligent ranking of sections of CPGs based on evidence using one or more processors. One or more clinical practice guidelines (CPGs) may be analyzed. A score may be assigned to one or more sections of the CPGs according evidential data identified in one or more data sources. The one or more sections of the CPGs may be ranked according to the scoring.

Figure 4:
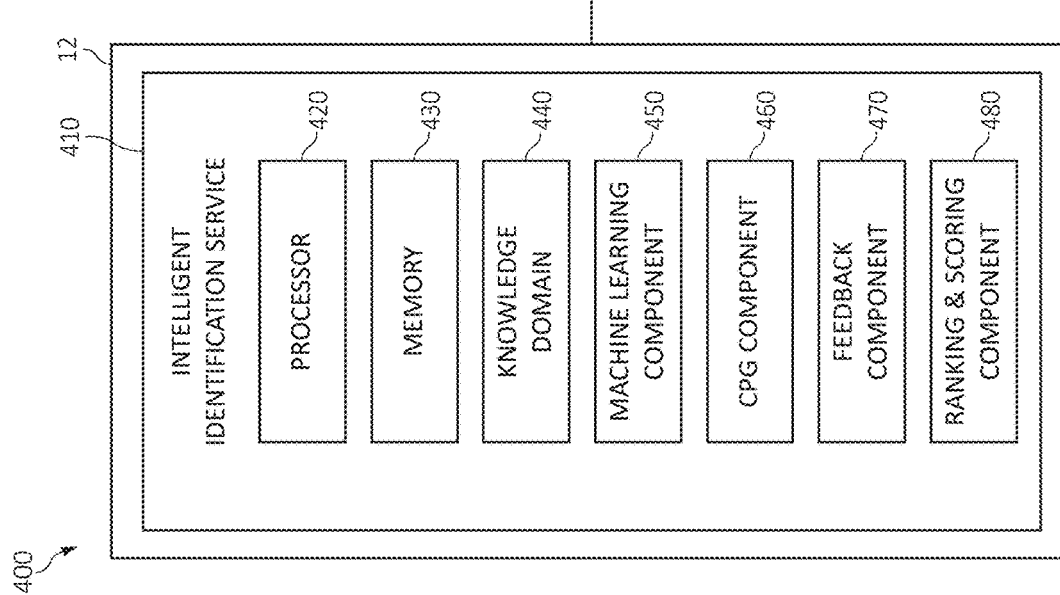
FIG. 4 is an additional block diagram depicting an exemplary functional relationship between various aspects of the present invention.

Turning now to FIG. 4, a block diagram depicting exemplary functional components 400 according to various mechanisms of the illustrated embodiments is shown. FIG. 4 illustrates intelligent ranking of sections of CPGs workloads and functions and training of a machine-learning model in a computing environment, such as a computing environment 402, according to an example of the present technology. As will be seen, many of the functional blocks may also be considered "modules" or "components" of functionality, in the same descriptive sense as has been previously described in FIGS. 1-3.

With the foregoing in mind, the module/component blocks of computing system 400 may also be incorporated into various hardware and software components of a system for intelligent ranking of sections of CPGs based on evidence in accordance with the present invention. Many of the functional blocks 400 may execute as background processes on various components, either in distributed computing components, or on the user device, or elsewhere.

An intelligent ranking system 410 is shown, incorporating processing unit 420 ("processor") to perform various computational, data processing and other functionality in accordance with various aspects of the present invention. The intelligent ranking system 410 may be provided by the computer system/server 12 of FIG. 1. The processing unit 420 may be in communication with memory 430. The intelligent ranking system 410 may also include a knowledge domain 440, machine learning component 450, a feedback component 470, a matching component 480.

In one aspect, the intelligent ranking system 410 may provide virtualized computing services (i.e., virtualized computing, virtualized storage, virtualized networking, etc.). More specifically, the intelligent ranking system 410 may provide virtualized computing, virtualized storage, virtualized networking and other virtualized services that are executing on a hardware substrate.

In one aspect, the knowledge domain 440 may be a database, which may also be an ontology of concepts representing a domain of knowledge and one or more data sources (e.g., documents, text, books, articles, journals, etc.). A thesaurus or ontology may be included in the knowledge domain 440 and may also be used to identify languages (types and rules relating to the language), grammar rules/policies, syntax rules, speech patterns, semantic relationships, and cultural speech patterns/rules/customers, and/or various dialects of a particular region. In one aspect, the term "domain" is a term intended to have its ordinary meaning. In addition, the term "domain" may include an area of expertise for a system or a collection of material, information, content and/or other resources related to a particular subject or subjects. A domain can refer to information related to any particular subject matter or a combination of selected subjects.

The term ontology is also a term intended to have its ordinary meaning. In one aspect, the term ontology in its broadest sense may include anything that can be modeled as an ontology, including but not limited to, taxonomies, thesauri, vocabularies, and the like. For example, an ontology may include information or content relevant to a domain of interest or content of a particular class or concept. The ontology can be continuously updated with the information synchronized with the sources, adding information from the sources to the ontology as models, attributes of models, or associations between models within the ontology.

Additionally, the domain knowledge may include one or more external resources such as, for example, links to one or more Internet domains, webpages, and the like. Additionally, the knowledge domain 440 may include data that may be received, updated, and/or communicated in real-time to and/or from one or more domain experts. For example, the feedback component 470 may receive real-time feedback from one or more domain experts and the feedback data may be maintained, stored, and/or updated in the knowledge domain 440.

In one aspect, the clinical practice guideline (CPG) component 460, in association with the ranking and scoring component 480, may assign a score to one or more sections of clinical practice guidelines (CPGs) according evidential data identified in one or more data sources and rank the one or more sections of the CPGs according to the scoring.

The CPG component 460 may analyze the one or more sections of the CPGs in one or more data sources. The CPG component 460 may dynamically associate the score of the one or more sections of the CPGs according to evidences identified in one or more data sources. The CPG component 460 may define the evidential data to include text data, media data, quantitative data approving or disapproving the one or more sections of the CPGs. The evidential data is located within the one or more data sources.

The ranking and scoring component 480 may determine the score of the one or more sections of the CPGs according to the evidential data. In one aspect, the score of the one or more sections of the CPGs indicates a level of positive evidentiary support or negative evidentiary support for the one or more sections of the CPGs.

The machine learning component 450 may learn the one or more CPG models and the evidential data associated with the one or more sections of the CPGs. The machine learning component 450, in association with the feedback component, may collect and use feedback data in relation to the ranking the one or more sections of the CPGs according to the scoring and adjust the ranking of the one or more sections of the CPGs according to the scoring.

The CPG component 460 may provide a notification indicating a change or modification to the score or a ranking of the one or more sections of the CPGs based on the evidential data.

The feedback component 470 may collect and use feedback data to adjust the scoring and/or the ranking of one or more sections of the CPG models and assist with a machine learning operation. The machine learning component 450 may use the knowledge domain 440 to use and/or analyze feedback data collected from one or more domain experts, patient profiles, historical feedback, or a combination thereof to (a) adjust/improve the rankings and scoring of one or more sections of CPGs based on one or more data sources (e.g., evidentiary data).

Returning to the CPG component 460, the CPG component 460 may apply the ranking of the one or more sections of the CPGs in a data source such as, for example an exemplary GCP 475 based on the evidential data. For example, the exemplary CPG 475 (e.g., a CPG with ranked sections based on evidences collected) may be provided with the various sections of the CPG scored based on the evidentiary data that supports or disproves the sections of the CPG. For example, a first sections of the CPG 475 is assigned a score of 72% representing a percentage for evidentiary support of that particular section, a second section of the CPG 475 is assigned a score of 53% representing a percentage for evidentiary support of that particular section, a third section of the CPG 475 is assigned a score of 17% representing a percentage for evidentiary support of that particular section, a fourth section of the CPG 475 is assigned a score of 85% representing a percentage for evidentiary support of that particular section, and a fifth section of the CPG 475 is assigned a score of 67% representing a percentage for evidentiary support of that particular section.

In one aspect, the various machine learning operations of the machine learning component 450, as described herein, may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, backpropagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are within the scope of this disclosure. Also, when deploying one or more machine learning models, a computing device may be first tested in a controlled environment before being deployed in a public setting. Also even when deployed in a public environment (e.g., external to the controlled, testing environment), the computing devices may be monitored for compliance.

In one aspect, the intelligent ranking system 410 may perform one or more calculations according to mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.) Thus, as used herein, a calculation operation may include all or part of the one or more mathematical operations.

Figure 5:
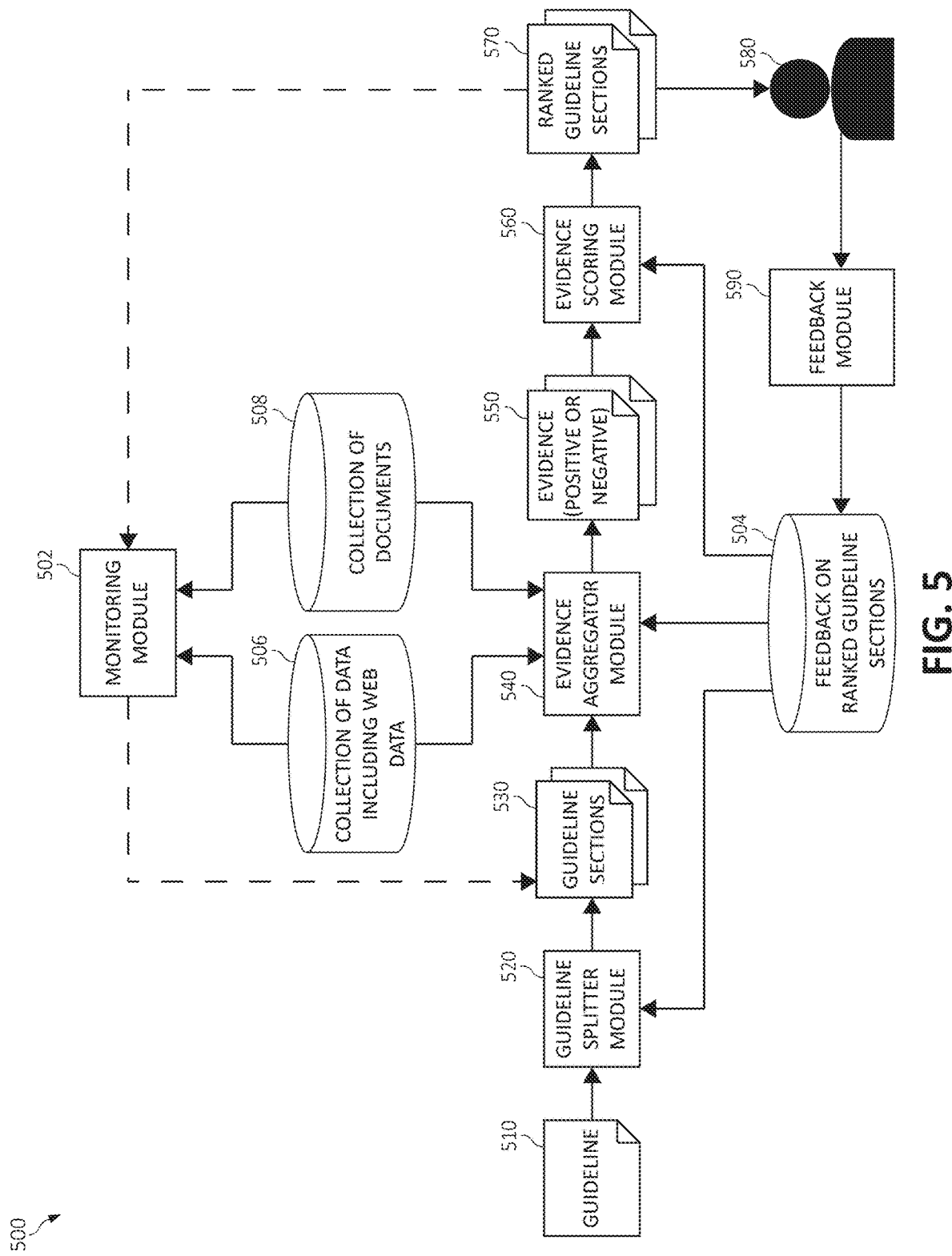
FIG. 5 is an additional block diagram depicting intelligent ranking of sections of clinical practice guidelines in which aspects of the present invention may be realized.

Turning now to FIG. 5, a block diagram of exemplary functionality 500 of an intelligent ranking of sections of CPGs is depicted. As will be seen, many of the functional blocks may also be considered "modules" or "components" of functionality, in the same descriptive sense as has been previously described in FIGS. 1-3.

As shown, the various blocks of functionality are depicted with arrows designating the blocks' 500 relationships with each other and to show process flow of an intelligent ranking of sections of CPGs based on evidence. Additionally, descriptive information is also seen relating each of the functional blocks 500. As will be seen, many of the functional blocks may also be considered "modules" or "components" of functionality, in the same descriptive sense as has been previously described in FIGS. 1-5. With the foregoing in mind, the module blocks 500 may also be incorporated into various hardware and software components of a system in accordance with the present invention. Many of the functional blocks 500 may execute as background processes on various components, either in distributed computing components, or on the user device, or elsewhere, and generally unaware to the user performing generalized tasks of the present invention.

Starting with block 502, one or more CPGs may be selected and provided to a guideline splitter module 520. The guideline splitter module 520 may analyze text data of one or more one or more CPGs (e.g., a CPG document) and divides/splits the one or more CPGs into sections. Each section of the one or more CPGs may consist of one or more paragraphs that are logically/semantically correlated.

In one aspect, a CPG may include a predefined structure, and the guideline splitter module 520 functions as a parser for that structure. The predefined structure may include constraints to guide a search for evidence (e.g., search for an age over 65 and cardiovascular disease). In an additional aspect, the guideline splitter module 520 may use a topic extraction operation (e.g., latent Dirichlet allocation "LDA" topic model) together with word embeddings (e.g., word2vec) to identify sections of the one or more CPGs with a certain probability. This can be achieved by ingesting a data source (e.g., a corpus of text for a specific CPG) and applying pre-processing techniques (e.g., lemmatization, tokenization, etc.) and running an LDA to identify key topic terms. A word embeddings model may be created on the same data source (e.g., the same corpus of text) and may be used to query a "bag-of-terms" nearest to those topic terms. The resulting bag-of-terms may have an associated topic term and may become a portion of a guideline and section of the CPG such as, for example, CPG sections 530 (e.g., guideline sections) and may be determined in this way with a defined degree of certainty and accuracy.

In an additional aspect, the guideline splitter module 520 receives as input feedback such as, for example, feedback on ranked sections of the CPGs in block 504, which is received from a feedback module 590 previously collected from a domain expert 580. Such feedback may be used to improve the results of the guideline splitter module 520.

An evidence aggregator module 540 may receive as input, from the guideline splitter module 520, sections of a guideline (e.g., CPG sections 530), and collections of documents 508 and data 506 (e.g., collection of data including internet/website data) to retrieve evidence for that particular CPG section 530. The collection of data 506 and data 508 may be used to identify, locate, search, and extract "evidence" or "evidentiary information/data."

Should the CPG sections 530 have specific structure, including constraints, the evidence aggregator module 540 may exploit them (e.g., age over 65 and cardiovascular disease) and used to guide the search. The evidence aggregator module 540 may classify each evidence 550 as positive (e.g., substantiating a section of the CPG such as, for example, the "CPG sections 530") or negative (e.g., disproving a section of the CPG such as, for example, the "CPG sections 530").

In an additional aspect, the evidence aggregator module 540 may use one or more various types of data/information retrieval operations. For example, the evidence aggregator module 540 may 1) automatically generate systematic reviews of a scientific field, 2) use a medical literature database search tool, and/or one or more instances of Artificial Intelligence ("AI") (e.g., AI instances for oncology and genomics). These AI instances may include IBM® Watson®. (IBM Watson are trademarks of International Business Machines Corporation).

In an additional aspect, the classification of the evidence 550 (positive/negative) by the evidence aggregator module 540 may be performed using a machine learning classification algorithm (e.g., support vector machines) or an artificial neural network ("ANN").

In an additional aspect, the evidence aggregator module 540 may also receive as input as input feedback such as, for example, feedback on ranked sections of the CPGs in block 504, which is received from a feedback module 590 previously collected from a domain expert 580. Such feedback may be used to improve the results of the evidence aggregator module 540.

An evidence scoring module 560 may receive as input, from the evidence aggregator module 540, the evidence 550 for each section of one or more CPGs (e.g., the positive/negative evidence for a section of a guideline) and produces, generates, determines, and/or calculates a score for each section of one or more CPGs. The evidence scoring module 560 may use the score to rank each section of one or more CPGs (e.g., the ranked guideline sections 570).

In one aspect, the score may be a real number, a numerical value within a range of values (e.g. [0, 1]), and/or a percentage value. In one aspect, each positive evidence may be considered and indicated, for example, as an "upvote" (e.g., a yes vote for approving the section as positive support), and each negative evidence as a "downvote" (e.g., a no vote for disapproving the section as negative support), and/or using a Wilson value. Also, other scoring means/operations may be used. In one aspect, a machine learning operation may be used to rank each section of one or more CPGs. The evidence scoring module 560 may also receive as input feedback such as, for example, feedback on ranked sections of the CPGs in block 504, which is received from a feedback module 590 previously collected from a domain expert 580. Such feedback may be used to improve the results of the evidence scoring module 560.

The feedback module 590 enables a domain expert to provide feedback on the ranked sections of a guideline (e.g., the ranked guideline sections 570). The feedback may include: 1) a vote (e.g., an integer value in the range [1, 5], with 5 being the best value) indicating a level of consistency of the section of the guideline. Said differently, the vote provides an indication of the degree of accuracy for identifying a given section of a guideline. A vote (e.g., an integer value in the range [1, 5] and 5 being the best value) may indicate an agreement/disagreement with a score/ranking of the given section of guideline. An indication of the quality/trust of the evidence may be an integer value in the range [1, 5] with 5 being the best value). In one aspect, the feedback module 590 consists of a user interface (e.g., a graphical user interface "GUI" connected to the internet) with a backend application.

In one aspect, the monitoring module 502 monitors any modification, adjustments, updates, changes, and/or updates in the collections of data 508 (e.g., including web data ("C1") and the collections of documents 506 ("C2"). When an item is added, deleted, changed, and or adjusted/updated in C1 or C2, the monitoring module 502 may trigger a re-computation for already/previously ranked sections of CPGs, and if the ranking of their sections changes, then the user is notified, and can again provide feedback on the new ranking.

Figure 6:
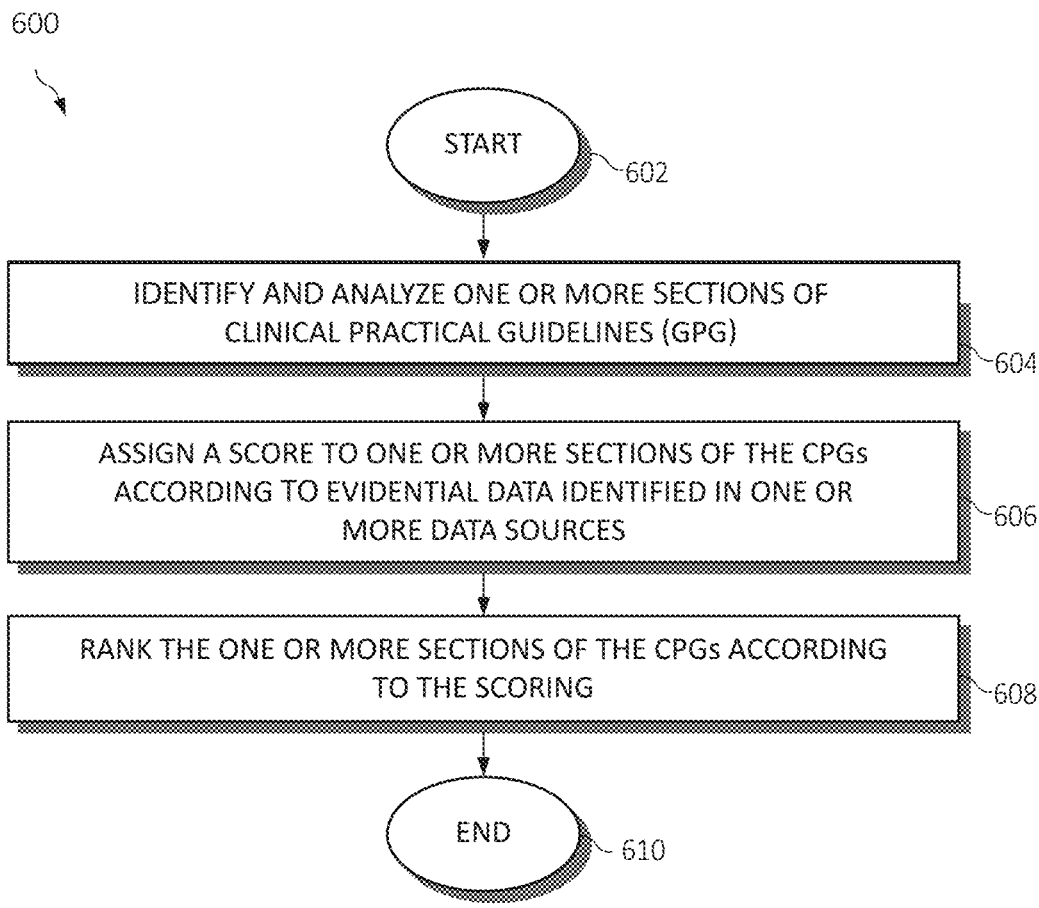
FIG. 6 is an additional flowchart diagram depicting an additional exemplary method for implementing intelligent ranking of sections of clinical practice guidelines based on evidence by a processor, again in which aspects of the present invention may be realized.

Turning now to FIG. 6, a method 600 for implementing intelligent ranking of sections of clinical practice guidelines by a processor is depicted, in which various aspects of the illustrated embodiments may be implemented. The functionality 600 may be implemented as a method executed as instructions on a machine, where the instructions are included on at least one computer readable medium or one non-transitory machine-readable storage medium. The functionality 600 may start in block 602.

One or more sections of clinical practice guidelines (CPGs) may be identified and analyzed, as in block 604. A score may be assigned to one or more sections of the CPGs according to evidential data identified in one or more data sources, as in block 606. The one or more sections of the CPGs may be ranked according to the scoring, as in block 608. The functionality 600 may end, as in block 610.

In one aspect, in conjunction with and/or as part of at least one block of FIG. 6, the operations of method 600 may include each of the following. The operations of method 600 may analyze the one or more sections of the CPGs in one or more data sources. The operations of method 600 may dynamically associate the score of the one or more sections of the CPGs in one or more data sources.

The operations of method 600 may define the evidential data to include text data, media data, quantitative data approving or disapproving the one or more sections of the CPGs. The evidential data is located within the one or more data sources.

The operations of method 600 may determine the score of the one or more sections of the CPGs according to the evidential data, wherein the score of the one or more sections of the CPGs indicates a level of positive evidentiary support or negative evidentiary support for the one or more sections of the CPGs.

The operations of method 600 may initialize a machine learning mechanism to, in addition to other operations: 1) learn the one or more CPG models and the evidential data associated with the one or more sections of the CPGs, 2) collect and use feedback data in relation to the ranking of the one or more sections of the CPGs according to the scoring, and/or 3) adjust the ranking of the one or more sections of the CPGs according to the scoring.

The operations of operations of method 600 may provide a notification indicating a change or modification to the score or a ranking of the one or more sections of the CPGs based on the evidential data.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for implementing intelligent ranking of sections of clinical practice guidelines by a processor, comprising:
   receiving a selection, via a user interface of a computing device, of one or more clinical practice guidelines (CPGs) as text data;
   executing machine learning logic to analyze the one or more CPGs to generate one or more CPG models, wherein generating the one or more CPG models includes splitting the one or more CPGs into one or more sections of the CPGs based on a correlation of the text data between the one or more sections of the CPGs, and wherein the splitting of the one or more CPGs into the one or more sections of the CPGs includes:
   ingesting the text data from a data source,
   performing a topic extraction operation on the text data to identify key topic terms,
   generating a word embeddings model of the text data,
   performing a query of a bag-of-terms nearest to the key topic terms, and
   generating the one or more sections of the CPGs according to an output of the query;
   subsequent to receiving the selection of the one or more CPGs, retrieving evidential data for the one or more CPGs from a plurality of data sources by parsing each of the plurality of data sources to identify and extract the evidential data relevant to the one or more CPGs among irrelevant data to the one or more CPGs in the plurality of data sources, wherein retrieving the evidential data includes automatically generating systematic reviews of a particular field of the one or more CPGs, using database search tools to perform the parsing, and instantiating instances of Artificial Intelligence (AI) logic by the machine learning logic to identify and analyze the evidential data;
   assigning a score to the one or more sections of CPGs according to the evidential data identified in the plurality of data sources;
   ranking the one or more sections of the CPGs according to the scoring; and
   outputting, via the user interface of the computing device, the ranking of the one or more sections of the CPGs according to the scoring.

2. The method of claim 1, further including identifying and analyzing the one or more sections of the CPGs in the plurality of data sources.

3. The method of claim 1, further including dynamically associating, during the generating of the one or more CPG models, the score of the one or more sections of the CPGs according to evidential data identified in the plurality of data sources.

4. The method of claim 1, wherein the score of the one or more sections of the CPGs indicates a level of positive evidentiary support or negative evidentiary support for the one or more sections of the CPGs.

5. The method of claim 1, further including defining the evidential data to include at least one of text data, media data, and quantitative data proving or disproving the one or more sections of the CPGs.

6. The method of claim 1, further including executing the machine learning logic to:
   collect and use feedback data in relation to the ranking the one or more sections of the CPGs according to the scoring; and
   adjust the ranking of the one or more sections of the CPGs according to the scoring.

7. The method of claim 1, further including providing a notification indicating a change or modification to the score or the ranking of the one or more sections of the CPGs based on the evidential data.

8. A system for implementing intelligent ranking of sections of clinical practice guidelines, comprising:
one or more computers with executable instructions that when executed cause the system to:
receive a selection, via a user interface of a computing device, of one or more clinical practice guidelines (CPGs) as text data;
execute machine learning logic to analyze the one or more CPGs to generate one or more CPG models, wherein generating the one or more CPG models includes splitting the one or more CPGs into one or more sections of the CPGs based on a correlation of the text data between the one or more sections of the CPGs, and wherein the splitting of the one or more CPGs into the one or more sections of the CPGs includes:
ingesting the text data from a data source,
performing a topic extraction operation on the text data to identify key topic terms,
generating a word embeddings model of the text data,
performing a query of a bag-of-terms nearest to the key topic terms, and generating the one or more sections of the CPGs according to an output of the query;
subsequent to receiving the selection of the one or more CPGs, retrieve evidential data for the one or more CPGs from a plurality of data sources by parsing each of the plurality of data sources to identify and extract the evidential data relevant to the one or more CPGs among irrelevant data to the one or more CPGs in the plurality of data sources, wherein retrieving the evidential data includes automatically generating systematic reviews of a particular field of the one or more CPGs, using database search tools to perform the parsing, and instantiating instances of Artificial Intelligence (AI) logic by the machine learning logic to identify and analyze the evidential data;
assign a score to the one or more sections of CPGs according to the evidential data identified in the plurality of data sources;
rank the one or more sections of the CPGs according to the scoring; and
output, via the user interface of the computing device, the ranking of the one or more sections of the CPGs according to the scoring.

9. The system of claim 8, wherein the executable instructions identify and analyze the one or more sections of the CPGs in the plurality of data sources.

10. The system of claim 8, wherein the executable instructions dynamically associate, during the generation of the one or more CPG models, the score of the one or more sections of the CPGs according to evidential data identified in the plurality of data sources.

11. The system of claim 8, wherein the score of the one or more sections of the CPGs indicates a level of positive evidentiary support or negative evidentiary support for the one or more sections of the CPGs.

12. The system of claim 8, wherein the executable instructions define the evidential data to include at least one of text data, media data, and quantitative data proving or disproving the one or more sections of the CPGs.

13. The system of claim 8, wherein the executable instructions execute the machine learning logic to:
collect and use feedback data in relation to the ranking the one or more sections of the CPGs according to the scoring; and
adjust the ranking of the one or more sections of the CPGs according to the scoring.

14. The system of claim 8, wherein the executable instructions provide a notification indicating a change or modification to the score or the ranking of the one or more sections of the CPGs based on the evidential data.

15. A computer program product for implementing intelligent ranking of sections of clinical practice guidelines by a processor, the computer program product comprising a non-transitory computer-readable storage medium having computer-readable program code portions stored therein, the computer-readable program code portions comprising:
an executable portion that receives a selection, via a user interface of a computing device, of one or more clinical practice guidelines (CPGs) as text data;
an executable portion that executes machine learning logic to analyze the one or more CPGs to generate one or more CPG models, wherein generating the one or more CPG models includes splitting the one or more CPGs into one or more sections of the CPGs based on a correlation of the text data between the one or more sections of the CPGs, and wherein the splitting of the one or more CPGs into the one or more sections of the CPGs includes:
ingesting the text data from a data source,
performing a topic extraction operation on the text data to identify key topic terms,
generating a word embeddings model of the text data,
performing a query of a bag-of-terms nearest to the key topic terms, and generating the one or more sections of the CPGs according to an output of the query;
an executable portion that, subsequent to receiving the selection of the one or more CPGs, retrieves evidential data for the one or more CPGs from a plurality of data sources by parsing each of the plurality of data sources to identify and extract the evidential data relevant to the one or more CPGs among irrelevant data to the one or more CPGs in the plurality of data sources, wherein retrieving the evidential data includes automatically generating systematic reviews of a particular field of the one or more CPGs, using database search tools to perform the parsing, and instantiating instances of Artificial Intelligence (AI) logic by the machine learning logic to identify and analyze the evidential data;
an executable portion that assigns a score to the one or more sections of CPGs according to the evidential data identified in the plurality of data sources;
an executable portion that ranks the one or more sections of the CPGs according to the scoring; and
an executable portion that outputs, via the user interface of the computing device, the ranking of the one or more sections of the CPGs according to the scoring.

16. The computer program product of claim 15, further including an executable portion that identifies and analyzes the one or more sections of the CPGs in the plurality of data sources.

17. The computer program product of claim 15, further including an executable portion that dynamically associates, during the generation of the one or more CPG models, the score of the one or more sections of the CPGs according to evidential data identified in the plurality of data sources.

18. The computer program product of claim 15, further including an executable portion that defines the evidential data to include at least one of text data, media data, and quantitative data proving or disproving the one or more sections of the CPGs, wherein the score of the one or more sections of the CPGs indicates a level of positive evidentiary support or negative evidentiary support for the one or more sections of the CPGs.

19. The computer program product of claim 15, further including an executable portion that executes the machine learning logic to:
- collect and use feedback data in relation to the ranking the one or more sections of the CPGs according to the scoring; and
- adjust the ranking of the one or more sections of the CPGs according to the scoring.

20. The computer program product of claim 15, further including an executable portion that provides a notification indicating a change or modification to the score or the ranking of the one or more sections of the CPGs based on the evidential data.

\* \* \* \* \*